Figure 1:
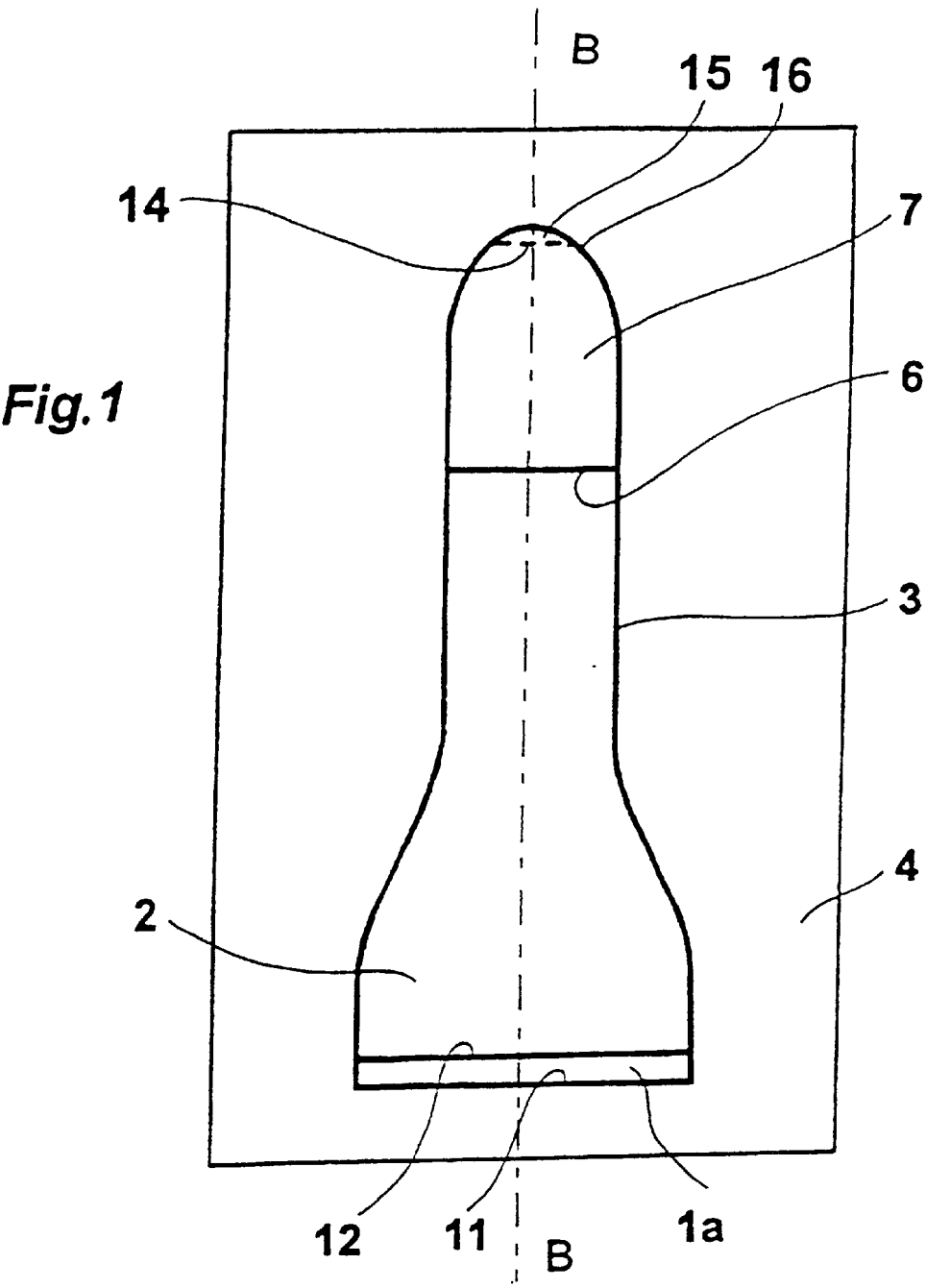

United States Patent [19]
Weilandt

[11] Patent Number: 6,051,293
[45] Date of Patent: Apr. 18, 2000

[54] PROBE SHEATH

[75] Inventor: Anders Weilandt, Sollentuna, Sweden

[73] Assignee: Amedic AB, Sweden

[21] Appl. No.: 09/051,697

[22] PCT Filed: Oct. 4, 1996

[86] PCT No.: PCT/SE96/01259

§ 371 Date: Jun. 26, 1998

§ 102(e) Date: Jun. 26, 1998

[87] PCT Pub. No.: WO97/14369

PCT Pub. Date: Apr. 24, 1997

[30] Foreign Application Priority Data

Oct. 17, 1995 [SE] Sweden .................................. 9503627

[51] Int. Cl.$^7$ ............................. B65D 85/38; G01K 1/08
[52] U.S. Cl. ........................ 428/35.2; 428/137; 428/192; 428/195; 206/305; 206/363; 383/211; 374/209
[58] Field of Search .................................. 428/35.2, 35.5, 428/130, 192, 195, 211, 200, 202, 137; 206/305, 306, 363; 374/158, 209; 383/210, 211

[56] References Cited

U.S. PATENT DOCUMENTS

| | | | |
|---|---|---|---|
| 3,732,975 | 5/1973 | Poncy | 206/306 |
| 3,759,370 | 9/1973 | Baltz | 374/158 |
| 4,136,776 | 1/1979 | Poncy | 206/306 |
| 4,351,616 | 9/1982 | Farnstrom et al. | 374/209 |
| 4,614,442 | 9/1986 | Poncy | 206/306 |
| 4,684,018 | 8/1987 | Järund | 206/306 |
| 5,069,337 | 12/1991 | Bala | 206/306 |
| 5,107,988 | 4/1992 | Bala | 206/306 |
| 5,332,092 | 7/1994 | Fischer | 206/305 |
| 5,795,632 | 8/1998 | Buchalter | 428/35.2 |

*Primary Examiner*—Rena L. Dye
*Attorney, Agent, or Firm*—Ostrolenk, Faber, Gerb & Soffen, LLP

[57] ABSTRACT

The present invention relates to a protective sheath (cover) for a probe for therapeutic or diagnostic use, in particular an aseptic disposable sheath aiming to protect the probe from body fluids and to protect contamination, and the patient and nursing personnel from the transmission of pathogenic microorganisms.

21 Claims, 1 Drawing Sheet

PROBE SHEATH

AREA OF THE INVENTION

The present invention relates to a protective sheath (cover) for a probe for therapeutic or diagnostic use, in particular an aseptic disposable sheath aiming to protect the probe from body fluids and to protect contamination, and the patient and nursing personnel from the transmission of pathogenic mircoorganisms.

BACKGROUND OF THE INVENTION

In medical care various types of probes for diagnostic or therapeutic purposes are used. For instance, probes intended for oral insertion in bronchoscopy, for rectal insertion for examination of the colon or for vaginal insertion for examination of the uterus. These probes comprise transmitters for various types of radiation, for instance, ultrasound or micro waves.

Probes are intended for long term use and examination of a large number of patients. In order to reduce the time consumed in preparing a used probe for the next examination, it is known to provide the probe with a removable cover of a polymer or similar material that can be disposed upon use. The sheath is designed in a way as to cover the parts of the probe coming into contact with body fluids and tissues. For instance, the sheath can have a form similar to a condom, i.e., in principle, the form of a finger with an opening at its base for insertion of the probe. 'Having the form of a finger' signifies tubular covers of various length having an insertion opening in their one end and a more or less blunt opposite end (top end) in the direction of which the cover may taper. This prevents contamination of the probe proper and transmission of contamination to the next patient or nursing personnel. A change of cover suffices for preparing the probe for the next use. To make the probe function properly, it is essential for the sheath covering the probe to adopt the form or the latter thus to make as much contact with the probe as possible.

The known protective sheaths can however be improved in regard of their simplicity and safety in use, that is, the ease with which they may be mounted on the probe and their contact with the probe.

DESCRIPTION OF THE INVENTION

The present invention relates to a protective sheath of the aforementioned kind which has improved properties in regard to the mounting and/or abutment, and thus function.

According to the invention, there is disclosed a substantially finger formed probe cover of the aforementioned kind provided mounted on a porous support and comprising a flat lower cover portion abutting against the support and being wholly or partially fixed at its border zone to the support in a way so as to enable it to be peeled off, and having a flat upper cover portion abutting against the lower cover portion and being congruent with it except at the insertion area, the lower cover portion at its insertion area being not covered by the upper cover portion and being fixed to the upper cover portion at its border zone congruent in form.

It is preferred for the protective sheath to have, at its top end, a chamber which can be opened from the base end side and which is filled with a liquid or gelatinous contact means, said chamber being formed by a transverse connection of the upper and lower cover portions, said connection being executed for being opened (broken) upon insertion of a probe into the sheath. Preferably the contact means is a liquid or a gel with appropriate optical and/or acoustical properties.

It is furthermore preferred for the cover thickness to be from 00.1 mm–0.1 mm, in particular from 0.02 to 0.05 mm.

It is also important for the protective sheath to have appropriate gliding properties in regard of its inside (the side facing the probe) and of its outside (the side facing the body). It is also preferred that one or both sides of the cover are treated with lubricating means; for instance, it is appropriate to silanize the outside or to cover it with a thin layer of polyurethane swellable in water, or with a similar covering. For the inside of the sheath simpler dry gliding means can also be used, such as talcum. Various known sterilization techniques can be used, such as radiation sterilization or ethylene oxide sterilization.

The abutment of the sheath against the probe can be improved by making the cover elastic and by preferably also providing it with a certain amount of non-elastic extendability. Suitable materials for such covers are certain types of polymers; a second choices are latex and synthetic rubber.

Figure 2:
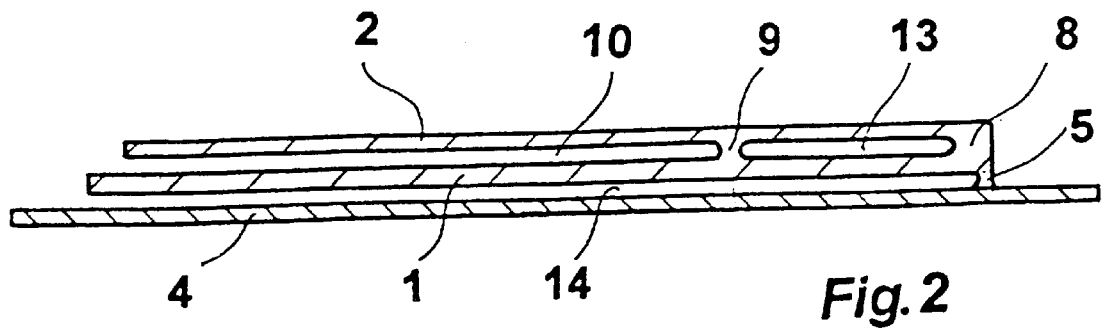

Further advantages of the invention will become apparent from the following detailed description of two preferred embodiments and a drawing joined to the description, of which FIG. 1 shows a top view of a probe cover fixed to a support, and FIG. 2 shows the same probe cover in section B—B (FIG. 1), the thickness of the layers being exaggerated for reason of clarity.

The first preferred embodiment of the invention relates to a protective probe cover or sheath of EMA copolymer (ethylene/polyacrylic acid), quality NCPE 540 Optene, thickness 0.025 mm.

In FIG. 1 this sheath is shown mounted on a support of thin paper 4 having a raw upper surface. In FIG. 1 the upper half 2 of the sheath covers the lower half except for a portion 1a at the sheath base. The edges of halves 1 and 2 coinciding in the top view are connected by welding in a circumferential border zone 3, except for the free edge section 12 of upper portion 2 being not congruent in form with the corresponding section 11 of lower portion 1. The connection of halves 1 and 2 in border zone 3 at 8 by welding (FIG. 2) is carried out with lower half 1 resting on support 4, whereby a weak welding connection (at 5; FIG. 2) of border zone 3 of sheath 1,2 to support 4 is also obtained.

In FIG. 2 the protective sheath is shown in section along line B—B (FIG. 1); along this line the combination of sheath and support is folded for storage, sheath 1,2 thus resting in a cover 4 of paper. For the sake of clarity the thickness of the polymer and paper layers has been much exaggerated. Loosely abutting portions are indicated by a small interstice, the first interstice being located between the upper 1 and the lower 2 polymer layer, and the interstice 14 between the last mentioned layer 1 and support 4. Sheath 1, 2 is fixed at support 4 only at the periphery (at 5) of border zone 3.

The cover or sheath is mounted on the probe by moving the free probe end (insertion end) in the direction of the freely accessible portion 1a of the lower half and then in direction of edge 12, whereat the halves of support 4 are folded by the operator's curved palm supporting 4 at its back side, thus displacing the opposite border zones 3 towards each other and tearing apart and enlarging the insertion opening at edge 12. Thereafter the probe is moved forward until it abuts against the corresponding end of cover 1,2. Upon use the cover can be easily drawn off by gripping flap 1a and moving it in the direction of the probe insertion end.

In certain applications it is essential to avoid the formation of air pockets between the probe and the cover while the cover is mounted on the probe. As a preventive measure a contact liquid or gel can be introduced into opening 12 prior to mounting. To avoid losses of liquid or gel these materials however can be advantageously disposed at the lower cover end section 7 in a chamber 13 formed by transverse partitioning of the cover at 9 by welding (heat or ultrasound). This welding connection is however, not made as permanent as welding connection 8 but rather in a way that it is easily broken upon cover 8 expanding during probe insertion.

In the second preferred embodiment executed in a similar manner, cover 1,2 can be open at the insertion end to provide for manipulation or inspection of tissue or similar elements by means disposed at said end. For instance, optical elements in combination with optically conducting fibres, gripping instruments of various kinds for sampling or operating purposes, cannulae, etc. all can be used. In this embodiment, the main part of the instrument is thus protected from contamination except for a small area at its tip. Such an opening is indicated in FIG. 1 by hatched section line 14 delimitating the opening. This embodiment thus lacks the cap 15. It is also possible to reinforce the material at the border zones of the front opening (at 16) to improve abutment reproducibility in the longitudinal direction of the probe cover 1,2. It is also possible to provide a front opening which initially is closed by a seal or a welding connection at 14 which can be broken, that is, a thin bridge of material which is broken during probe insertion or, possibly, by a means which can be telescoped from the probe tip, such as a pair of gripping tongs. In the last instance the probe is inserted into the patient fully protected, and the seal is only broken upon the probe having reached the desired position in the patient. The chamber formed by the two breakable seals 6, at 14, and the sheath portions located between them can be partially filled in a way as disclosed in connection with chamber 7.

I claim:

1. A protective sheath comprising:

a top end;

a base end including an insertion opening for a probe;

said sheath being mounted on a support;

a flat lower cover portion abutting against the support and being wholly or partially fixed at its edge zone to the support in a way so that the lower cover portion is detachably mounted to said support;

a flat upper cover portion abutting loosely against said lower cover portion and being congruent in form with said lower cover portion except at the insertion opening, said lower cover portion at the insertion opening not being covered by the upper cover portion thereby forming a free flap, said lower cover portion being fixed to the upper cover portion at its border zone a chamber disposed at the top end of the sheath, the chamber being accessible from the base end side, the chamber being filled with a liquid or gelatinous contact material, the chamber being formed by a transverse connection of the upper and the lower cover portions, the transverse connection being formed so that it is opened upon insertion of a probe into the sheath.

2. The protective sheath according to claim 1, wherein a resistance of the transverse connection against penetration is less than of the connection between the upper and lower cover portions in the border zone.

3. The protective sheath according to claim 1, wherein the contact material is a sterile gel.

4. The protective sheath according to claim 1, wherein the sheath has a thickness which is from 0.01 mm to 0.3 mm.

5. The protective sheath according to claim 1, wherein said sheath is treated with a lubricating means on at least one side.

6. The protective sheath according to claim 1, wherein said sheath is formed in a permanently extendable and elastic copolymer.

7. The protective sheath according to claim 1, wherein said support is comprised of a paper having a rough upper surface.

8. The protective sheath according to claim 1, wherein said sheath has an opening or a breakable seal at its top end.

9. The protective sheath according to claim 1, wherein a wall zone delimitating the insertion area is reinforced.

10. The protective sheath as claimed in claim 4, wherein said sheath has a thickness which is between 0.01 and 0.05 mm.

11. The protective sheath as claimed in claim 6, wherein said sheath is formed by an ethylene/acrylic copolymer.

12. A protective sheath comprising:

a top end;

a base end continuous with said top end and having an opening which is effective to receive a probe;

a chamber disposed in said top end, said chamber being defined by a cap of said top end, sides of said top end, and a seal disposed between said chamber and said base end.

13. The protective sheath as claimed in claim 12, further comprising:

an upper cover portion;

a lower cover portion fixed to said upper cover portion;

a support detachably mounted to said lower cover portion.

14. The protective sheath as claimed in claim 13, wherein said upper cover portion covers all of said lower cover portion except for a free edge section.

15. The protective sheath as claimed in claim 12, wherein said chamber contains a liquid disposed therein.

16. The protective sheath as claimed in claim 12, wherein said cap comprises a breakable seal.

17. The protective sheath as claimed in claim 12, wherein said seal is broken upon complete insertion of said probe.

18. A method of inserting a probe into a probe sheath, said method comprising:

inserting said probe into an opening of said probe sheath;

breaking a seal disposed within said probe sheath using said probe; and inserting said probe further in to said probe sheath.

19. The method as claimed in claim 18, wherein said breaking introduces a liquid, stored in a chamber of said probe sheath, on to said probe.

20. The method as claimed in claim 18, further comprising detaching said probe and said probe sheath from a support detachably connected to said probe sheath.

21. The method as claimed in claim 18, further comprising inserting said probe further through said probe sheath thereby breaking off a cap of said probe sheath.

* * * * *